(12) United States Patent
Egami

(10) Patent No.: US 8,431,512 B2
(45) Date of Patent: Apr. 30, 2013

(54) OXYCHLORINATION CATALYST AND METHOD FOR PREPARING THE SAME

(75) Inventor: Kazutaka Egami, Kitakyushu (JP)

(73) Assignee: JGC Catalysts and Chemicals Ltd., Kawasaki-Shi (JP)

( * ) Notice: Subject to any disclaimer, the term of this patent is extended or adjusted under 35 U.S.C. 154(b) by 1048 days.

(21) Appl. No.: 11/798,821

(22) Filed: May 17, 2007

(65) Prior Publication Data

US 2008/0248946 A1 Oct. 9, 2008

(51) Int. Cl.
*B01J 23/70* (2006.01)
(52) U.S. Cl.
USPC ........... 502/346; 502/225; 502/226; 502/231; 502/340; 502/341; 502/345; 570/243; 570/245; 570/224
(58) Field of Classification Search .................. None
See application file for complete search history.

(56) References Cited

U.S. PATENT DOCUMENTS

| | | | |
|---|---|---|---|
| 3,278,263 A * | 10/1966 | Cox | 423/607 |
| 2007/0112235 A1* | 5/2007 | Kramer et al. | 570/243 |
| 2009/0025375 A1* | 1/2009 | Poojary et al. | 60/295 |

FOREIGN PATENT DOCUMENTS

| | | | |
|---|---|---|---|
| JP | S45-39616 | | 12/1970 |
| JP | 11-090232 | | 4/1999 |
| JP | 11-090233 | | 4/1999 |
| JP | 11-090234 | | 4/1999 |
| JP | 2005-000730 | | 1/2005 |
| JP | 2005-000731 | * | 1/2005 |

OTHER PUBLICATIONS

JP 2005-000730 (machine translation), Date:Jan. 2005, Japan, Susumu et al. Classification B01J 27/125: "Method for preparing oxychloriniation catalyst and oxychlorination catalyst".*

* cited by examiner

*Primary Examiner* — Melvin C Mayes
*Assistant Examiner* — Smita Patel
(74) *Attorney, Agent, or Firm* — Manabu Kanesake

(57) ABSTRACT

A catalyst for oxychlorination according to the present invention contains alumina and copper, and a content of copper is in the range from 5 to 20% by weight calculated as that of CuO, while a content of halogen is not more than 5% by weight. The catalyst is produced by the following steps (a) to (c): (a) preparing a slurry for spray-drying by adding an acid and an aqueous solution of cupric nitrate in a pseudo-boehmite alumina slurry; (b) spray-drying the slurry; and (c) burning the particles obtained in step (b).

12 Claims, No Drawings

OXYCHLORINATION CATALYST AND METHOD FOR PREPARING THE SAME

TECHNICAL FIELD

The present invention relates to catalyst for oxychlorination and a method of manufacturing the same. More specifically, this invention relates to a catalyst for oxychlorination having high fluidity, excellent in the capability for suppressing lowering of the fluidity and abrasion resistance, and also having high activity, high selectivity for 1,2-dichloroethane (hereinafter, abbreviated as EDC) and high capability of suppressing ethylene combustion. The present invention also relates to a method of manufacturing the catalyst.

BACKGROUND TECHNOLOGY

For chlorination of aliphatic hydrocarbon by using means of oxychlorination, there has been used a catalyst in which a metal salt is carried on a carrier such as porous alumina, porous silica alumina or clay. Specifically for production of EDC by oxychlorination of ethylene for industrial purpose, there has been used a catalyst for a fluidized bed in which cupric chloride on is carried on an alumina carrier by the impregnation method. However, there has been the problem for such a catalyst that the activity and the fluidity are lowered due to migration or sublimation of copper as an activator component, and thereby, the selectivity for and the yield of the EDC is lowered since distribution of temperature in catalyst layers becomes inhomogeneous and then a combustion reaction of ethylene develops more in portions heated to at a high temperature. In order to suppress migration or sublimation of copper, and also to enhance the selectivity for the EDC, an alkaline metal, an alkaline-earth metal or a rare-earth metal is added to the catalyst.

On the other hand, there has been known a catalyst obtained by precipitating a carrier component and an activator component simultaneously (hereinafter, referred to as co-precipitation method), and then spray-drying the components (Refer to Patent document 1). Further, there has been known also a catalyst carrying an alkaline metal, an alkaline earth-metal or a rare-earth metal on a catalyst prepared by the co-precipitation method (Refer to Patent document 2, Patent document 3, and Patent document 4).

However, the problems of lowering the fluidity, the activity and the selectivity as described above can not be solved completely by theses catalysts.

The present inventors have disclosed a catalyst, which is obtained by using a pseudo-boehmite-alumina-slurry prepared in advance as an alumina source, and adding an activator component such as copper and promoter components such as an alkaline metal, an alkaline-earth metal or a rare-earth metal to the slurry, and then spray-drying the slurry. The catalyst can suppress lowering of the fluidity and also high activity and selectivity (Refer to Patent document 5 and Patent document 6).

However, the catalyst described above has the problem of corrosion of an apparatus used for manufacturing the catalyst because a large quantity of halogen (chlorine) is used in the process of manufacturing the catalyst. For instance, there has been the possibility of damaging the manufacturing apparatus due to corrosion of stainless steel and as a result causing leakage of gaseous halogen or reaction materials to outside of the system. On the other hand, the activity, selectivity and fluidity of the catalyst are insufficient when an amount of halogen (chlorine) used as a raw material decreases, or when other acidic salt such as sulfate is used.

Patent document 1: JP S45-39616 B
Patent document 2: JP HI 1-90232 A
Patent document 3: JP HI 1-90233 A
Patent document 4: JP HI 1-90234 A
Patent document 5: JP 2005-000730 A
Patent document 6: JP 2005-000731 A

DISCLOSURE OF THE INVENTION

The present inventors made strenuous efforts for solving the problems described above, and finally found the fact that, when a pseudo-boehmite alumina slurry prepared in advance is used as an alumina source, and then cupric nitrate is used in the manufacturing process of the catalyst, the problems corrosion of an apparatus used for manufacturing the catalyst and of leakage of gaseous halogen and reaction materials to outside of the system can be solved, and also that the catalyst obtained as described above shows the high activity and selectivity as those in the conventional catalysts. The inventors have achieved the present invention based on the findings.

The catalyst for oxychlorination according to the present invention contains alumina and copper, and a content of copper is in the range from 5 to 20% by weight calculated as CuO and a content of the halogen is 5% by weight or less.

Furthermore, the catalyst for oxychlorination according to the present invention contains an alkaline earth metal such as magnesium, and a content of the alkaline earth metal is preferably in the range from 0.1 to 6% by weight as an oxide base (MO: M denoting an alkaline earth element).

Furthermore, the catalyst for oxychlorination according to the present invention contains a rare earth element, and a content of the rare earth element is preferably in the range from 0.1 to 6% by weight as an oxide base ($RE_2O_3$: RE denoting a rare-earth element).

The catalyst for oxychlorination according to the present invention contains an alkaline element such as potassium, and a content of the alkaline element is preferably in the range from 0.1 to 3% by weight as oxide base ($N_2O$: N denoting an alkaline element).

The catalyst for oxychlorination described above can be produced through the following steps (a) to (c).
(a) A step of preparing slurry for spray-drying by adding an acid and an aqueous solution of cupric nitrate to a pseudo-boehmite-alumina-slurry.
(b) A step of spray drying the slurry described above.
(c) A step of calcining particles obtained in the step (b).

pH of the slurry for spray-drying is preferably in the range from 3 to. 5.

It is preferable that furthermore an aqueous solution of an alkaline earth salt is added to the slurry in the process (a).

It is preferable that furthermore an aqueous, solution of a rare earth salt is added to the slurry in the process (a).

It is preferable that furthermore an aqueous solution of an alkaline salt is added to the slurry in the process (a).

With the present invention, it is possible to provide a catalyst for oxychlorination which can solve the problems of corrosion of an apparatus for manufacturing the catalyst and scattering of halogen gas or the like into the atmospheric air, and also which can provide excellent activity, selectivity for EDC, capability for suppressing combustion of ethylene, and insure the fluidity stable for a long term and high abrasion resistance.

BEST MODE FOR CARRYING OUT THE INVENTION [Catalyst for Oxychlorination]

Catalyst for oxychlorination according to the present invention contains alumina and copper.

A content of copper calculated as that of CuO is preferably in the range from 5 to 20% by weight, and more preferably in the range from 8 to 15% by weight. When the content of copper is less than 5% by weight, the activity is insufficient, and a yield of EDC drops. When a content of copper in the catalyst is over 20% by weight, the feed ethylene is excessively burnt with the EDC yield dropped, and an amount of copper is excessive so that the copper migrates to external surfaces of the catalyst particles or sublimates, which in turn may lower the fluidity.

A content of halogen (chlorine) in the catalyst is preferably 5% by weight or less, preferably 2% by weight or less, and more preferably 0.5% by weight or less. When the content of halogen (chlorine) is over 5% by weight, the halogen cause corrosion of a device during a process of producing the catalyst, and the halogen gas may be exhausted to the atmospheric air when heated and burnt.

The catalyst for oxychlorination according to the present invention preferably contains an alkaline-earth element, and a contents of the alkaline-earth element calculated as that of an oxide thereof (MO: M denoting an alkaline-earth element) is preferably in the range from 0.1 to 6% by weight, and more preferably in the range from 0.2 to 4% by weight. When a content of the alkaline-earth element is less than 0.1% by weight, the bulk density and abrasion resistance of the obtained catalyst tend to become lower. When a content of the alkaline-earth element is over 6% by weight, a pore volume of the obtained catalyst becomes smaller, and the activity may be insufficient.

The alkaline-earth element is preferably magnesium, and when magnesium is used, a catalyst excellent in the abrasion resistance can be obtained without lowering the activity. A content of magnesium calculated as that of MgO is preferably in the range from 0.2 to 3.5% by weight.

Furthermore, the catalyst according to the present invention may contain alkali element, and a content of the alkali element calculated as that of an oxide thereof ($N_2O$:N denoting an alkali element) is preferably in the range from 0.1 to 3% by weight, and more preferably in the range from 0.2 to 2% by weight. When a content of the alkali element in the catalyst is less than 0.1% by weight, the effect of suppressing combustion of ethylene is insufficient, so that a yield of EDC becomes lower. When content of the alkali element is over 3% by weight, a reaction rate become lower with the EDC yield dropped.

The alkali element is preferably potassium, and when potassium element is used, oxidation of ethylene can easily be suppressed, without substantially lowering a reaction to give Cl generated via oxygen from hydrochloric acid to ethylene, which is a main reaction.

Furthermore, the catalyst according to the present invention may contain a rare-earth element, and a content of the rare-earth element calculated as that of an oxide thereof ($RE_2O_3$: RE denoting a rare-earth element) is preferably in the range from 0.1 to 6% by weight, and more preferably in the range from 0.2 to 4% by weight. When a content of the rare-earth element is less than 0.1% by weight, selectivity for EDC lowers, and also the effect of suppressing combustion of ethylene becomes insufficient, so that also a yield of EDC becomes lower. When a content of the rare-earth element is over 6% by weight, a reaction rate of Cl becomes lower, and the EDC yield drops.

A content of alumina in the catalyst according to the present invention calculated as that of $Al_2O_3$ is preferably in the range from 60 to 85% by weight, and more preferably in the range from 65 to 80% by weight. When a content of alumina is less than 60% by weight, a specific surface area and a pore volume of the catalyst become smaller, and at the same time the activator components or the like increases although the specific surface area and the pore volume are small, and sometimes the activity is not effectively shown. Furthermore, sometimes the abrasion resistance becomes insufficient. When a content of alumina is over 85% by weight, the activator component and/or promoter components such as the rare-earth elements and alkali elements decrease, and sometimes the activity or the selectivity becomes insufficient.

In the present invention, when the alumina is $\gamma$-$Al_2O_3$, the specific surface area and the pore volume of the catalyst become larger, so that the catalyst is excellent in durability as well as the activity and the selectivity.

An average diameter of the catalyst for oxychlorination according to the present invention is preferably in the range from 40 to 75 μm, and more preferably in the range from 45 to 70 μm. When the average diameter is less than 40 μm, the sufficient fluidity may not be obtained, or the catalyst loss may increase. When the average particle diameter is over 75 μm, the sufficient fluidity may not be obtained like in the case when the average diameter is too small.

Diameter of the particles are substantially distributed homogeneously, and it is preferable that a percentage of particles with the diameter of less than 30 μm is preferably 10% by weight or below, and a percentage of particles with the diameter over 90 μm is 20% by weight or below. If necessary, particles of catalyst may be classified in further different ranges.

The distribution of particle diameters can be decided by the micromesh sieve method.

A specific surface area of the catalyst is preferably in the range from 150 to 300 $m^2$/g, and more preferably in the range from 200 to 250 $m^2$/g. When the specific surface area is less than 150 $m^2$/g, the efficiency of addition reaction of Cl to ethylene becomes lower, and a yield of EDC which is a target product becomes lower. When the specific surface area is more than 300 $m^2$/g, sometimes oxidation of ethylene may become remarkable.

The pore volume of the catalyst is preferably in the range from 0.25 to 0.40 ml/g, and more preferably in the range from 0.30 to 0.35 ml/g. When the pore volume is less than 0.25 ml/g, also the specific surface area is low, and sometimes the yield of EDC may become lower. In addition, the bulk density may become higher and the fluidity during the reaction may become lower. When the pore volume is over 40 ml/g, the abrasion resistance becomes insufficient, and scattering of the catalyst during the reaction tends to increase.

A bulk or compact density of the catalyst (CBD) is preferably in the range from 0.90 to 1.20 g/ml, and more preferably in the range from 1.00 to 1.10 g/ml. When the bulk density (CBD) is less than 0.90 g/ml, the catalyst is too light, and sometimes the catalyst may scatter to outside of the reaction vessel. When the bulk density (CBD) is over 1.20 g/ml, sometimes the fluidity becomes insufficient, which in turn may cause combustion of ethylene due to a polarized flow or polarized heating within the reaction vessel.

The bulk density (CBD) can be obtained by filling a specified amount of the catalyst heated under prespecified conditions in ,a quantifying vessel (such as, for instance, a measuring cylinder), sufficiently vibrating the vessel, measuring a bulk volume in the most tightly filled state, and dividing the bulk volume by the amount of filled catalyst.

[Method of Producing a Catalyst for Oxychlorination]

A method of producing the catalyst for oxychlorination according to the present invention is described below.

The method of producing the catalyst for oxychlorination according to the present invention includes the following steps (a) to (c).

(a) Step of preparing slurry for spray-drying by adding an acid and an aqueous solution of cupric nitrate to pseudo-boehmite alumina slurry (b) Step of spray-drying the slurry, and (c) Step of calcining the particles obtained in step (b)

Step (a)

In the present invention, pseudo-boehmite is used as a source of alumina. The pseudo-boehmite ($Al_2O_3 \cdot nH_2O$, n:0.5 to 2.5) is one of crystalline alumina hydrates, and are ordinarily secondary fibrous particles formed with bundles of fibrous primary particles.

As for the dimensions of a primary particle of the pseudo-boehmite alumina, the average length ($L_1$) is preferably in the range from 1 to 10 nm, and the average width ($W_1$) is in the range from 0.5 to 3 nm. When the average length ($L_1$) is less than 1 nm, alumina is excessively dissolved, and the pore volume and the specific surface area of alumina finally obtained become smaller, and also the activity becomes insufficient. When the average length ($L_1$) is over 10 nm, the bulk density of the obtained catalyst becomes lower and the abrasion resistance is insufficient.

When the average width ($W_1$) is less than 0.5 nm, like in the case where the average length ($L_1$) is less than 1 nm, the pore volume and the specific surface area of alumina finally obtained become smaller, and also the activity becomes insufficient. When the average width ($W_1$) is over 3 nm, the bulk density of the obtained catalyst becomes lower and the abrasion resistance is insufficient.

Size of the primary particles can be determined by photographing the particles with a scanning electron microscope and visually observing the images.

The pseudo-boehmite alumina used in the present invention may be any of known one so long as the conditions for the pseudo-boehmite alumina as described above are satisfied.

The pseudo-boehmite alumina can be obtained, for instance, by reacting an aqueous solution of alkaline aluminum salt and an acidic substance to each other, cleaning and aging the reaction product according to the necessity. More specifically, alternatively the pseudo-boehmite alumina can be obtained by reacting an aqueous solution of sodium aluminate in a desired concentration range and an aqueous solution of aluminum sulfate at a desired weight ratio, cleaning the reaction product with water, and then aging the reaction product, if required.

A concentration of the pseudo-boehmite alumina used in the present invention is preferably in the range from 2 to 20% by weight, and more preferably in the range from 5 to 18% by weight, when calculated as that of $Al_2O_3$. When the concentration is less than 2% by weight, a concentration of the slurry for spray-drying is too low, and a percentage of too small particles against all of the obtained spherical particles becomes larger, and there occurs the troubles that the fluidity is low and the catalyst can not be captured with a cyclone and therefore loss of the catalyst increases. When a concentration of the pseudo-boehmite alumina slurry is over 20% by weight, a concentration of the slurry for spray-drying becomes too high, and there may occur the problems that the viscosity is too high and spray-drying is difficult, or that, even if spray-drying is possible, dispersibility of activator component becomes insufficient and properties of the obtained catalyst are insufficient or the abrasion resistance or the bulk density (CBD) are disadvantageously low.

In the present invention, at first an acid is added to the pseudo-boehmite alumina slurry as described above. The acid, which can be used in this step, includes mineral acids such as hydrochloric acid, nitric acid, sulfuric acid, and organic acids such as acetic acid. Of these acids, nitric acid is preferable, because the nitric acid can homogenize aggregated particles (secondary particles) in the pseudo-boehmite alumina slurry and a catalyst with high abrasion resistance and a high bulk density (CBD) can be obtained. Furthermore, when nitric acid is used, there is no possibility that a device is corroded during a process of producing the catalyst.

A quantity of added acid is preferably in the range from 0.001 to 0.1 moles, and more preferably in the range from 0.005 to 0.05 moles per mole of $Al_2O_3$ in the slurry. When the quantity of added acid is less than 0.001 moles, aggregated particles (secondary particles) in the pseudo-boehmite alumina slurry are kept inhomogeneous, which may disadvantageously lower the abrasion resistance and bulk density (CBD) of the obtained catalyst. Furthermore, pH of the alumina slurry may be over 6. In that case, most of copper added next or an alkaline-earth element or a rare-earth element added according to the necessity are deposited before spray-drying, so that the components can not homogeneously be scattered and deposited on the alumina carrier, and the activity, the effect of suppressing oxidation of ethylene, and a long term fluidity of the obtained catalyst may become lower. When an amount of added acid is more than 0.1 moles per mole of $Al_2O_3$, most of the pseudo-boehmite alumina and the added acid react with each other and are dissolved. In that case, a specific surface area and a pore volume of the obtained catalyst become lower and the activity may become insufficient.

A concentration of the acid used in the step above is generally in the range from 10 to 35% by weight.

pH of the pseudo-boehmite alumina slurry used in this step is generally in the range from 2 to 6, and preferably in the range from 3 to 5.

An aqueous solution of cupric sulfate is added.

An amount of the cupric sulfate aqueous solution added in the step above is adjusted so that a content of copper in the obtained catalyst is in the range from 5 to 20% by weight, and more preferably in the range from 10 to 15% by weight, when calculated at that of an oxide thereof (CuO). When a content of copper in the catalyst is less than 5% by weight, the activity is insufficient and a yield of EDC becomes lower. When a content of copper in the catalyst is over 20% by weight, combustion of feed ethylene proceeds excessively, and the EDC yield becomes lower, and a quantity of copper is excessive. In this case, copper may migrate to an external surface of the catalyst particles, which may cause sublimation or lowering of the fluidity.

In step (a), it is preferable that at least one of an aqueous solution of alkaline-earth salt, an aqueous solution of rare-earth salt, and an aqueous solution of alkali salt is added at the same time when or after the cupric nitrate aqueous solution is added.

As the alkaline-earth salts, any of nitrate, chlorate, sulfate and the like of such elements as magnesium, calcium, and barium may be used in this step. Especially, when a nitrate is used, corrosion of a device for production of the catalyst can be reduced, and it is possible to obtain a catalyst containing halogen only a little.

Especially, when magnesium nitrate is used, it is possible to obtain a catalyst with the activity not lowered and excellent in the abrasion resistance.

A quantity of the aqueous solution of alkaline-earth salt is adjusted so that a content of the alkaline-earth in the finally obtained catalyst is in the range from 0.1 to 6% by weight, and more preferably in the range from 0.2 to 4% by weight. When a content of the alkaline-earth is less than 0.1% by weight, the bulk density and abrasion resistance of the obtained catalyst tend to become lower. When a content of the alkaline-earth is over 6% by weight, sometimes the pore volume of the obtained catalyst becomes smaller with the activity becoming insufficient. When magnesium nitrate is used, preferably the quantity is adjusted so that a content of magnesium in the obtained catalyst as calculated as that of MgO is in the range from 0.2 to 3.5% by weight.

As the rare-earth salt, any of nitrate, chlorate, sulfate and the like of lanthanum, cerium, and the like may be used. Especially when nitrate is used, corrosion of a device used for production of a catalyst can be reduced, and it is possible to obtain a catalyst with a small content of halogen, excellent in selectivity for EDC, and capable of suppressing combustion of ethylene.

A quantity of aqueous solution of the rare-earth salt used in the step is adjusted so that a content of the rare-earth element in the catalyst finally obtained is in the range from 0.1 to 6% by weight, and more preferably in the range from 1 to 5% by weight. When a content of the rare-earth element is less than 0.1% by weight, the selectivity for EDC becomes lower, and also the effect of suppressing combustion of ethylene becomes insufficient, so that also a yield of EDC becomes lower. When a content of the rare-earth element is over 6% by weight, a reaction rate of Cl drops and the EDC yield becomes lower.

As the alkali salt, any of nitrate, chlorate, sulfate or the like of sodium, potassium, and the like may be used, and especially nitrate is preferable. When potassium nitrate is used, it is possible to obtain a catalyst with the small halogen content which is excellent in selectivity for EDC and capable of suppressing combustion of ethylene.

A quantity of aqueous solution of the alkali salt used in this step is adjusted so that a content of alkali in the catalyst finally obtained is in the range from 0.1 to 3% by weight, and more preferably in the range from 0.5 to 2% by weight. When a content of the alkali is less than 0.1% by weight, the effect of suppressing combustion of ethylene is insufficient, so that a yield of EDC becomes lower. When a content of the alkali is over 3% by weight, a reaction rate of Cl drops with the EDC yield dropped.

There is no specific restriction over a concentration of each aqueous solution, and generally an aqueous solution with the concentration in the range from 1 to 30% by weight is used. Furthermore, there is no specific restriction over an order of addition of the aqueous solutions. Each aqueous solution excluding aqueous solution of the alkali salt may be used as a form of a mixed aqueous solution. pH of the slurry for spray-drying prepared as described is in the range from 1.5 to 5.5, and more preferably in the range from 3 to 5. When pH is less than 1.5, the pseudo-boehmite alumina is dissolved excessively, and therefore a specific surface area and a pore volume of the obtained catalyst become lower, and the activity tends to become insufficient. When pH is over 5.5, copper may be deposited as a hydroxide before spray-drying is performed, so that the copper component can not homogenously be scattered and deposited on the alumina carrier, and therefore the activity and the long term fluidity tend to become lower.

A concentration of the slurry for spray-drying calculated as that of the solid phase is in the range from 5 to 25%, and more preferably in the range from 10 to 20% by weight. When the concentration is less than 5% by weight, an average diameter of the spherical particles obtained by spray-drying tends to become smaller, and a percentage of fine particles with the diameter of 20 μm or below may become larger, and also, because the moisture content is high, a large amount of thermal energy is required, which is not desirable from the economical point of view. When the concentration is over 25% by weight, viscosity of the slurry is too high, and sometimes the spray-drying can hardly be carried out.

It is to be noted that the slurry for spray-drying may be subjected to the processing for emulsification or for homogenizing with a homogenizer, a colloid mill, or the like.

Step (b)

The slurry for spray-drying obtained in step (a) is then spray-dried. There is no specific restriction over a method of spray-drying so long as a fluid catalyst having a form like a spherical particle like any known fluid catalyst for oxychlorination can be obtained. For instance, a spray-drying machine based on the disk rotation system, the nozzle system or the like may be used in a heated air flow.

In this step, a temperature of the heated air flow is in the range from 150 to 500° C., and more preferably in the range from 200 to 350° C. When a temperature of the heated air flow is less than 150° C., sometimes drying is performed insufficiently. When a temperature of the heated air flow is over 500° C., drying is performed rapidly, and sometimes the activator component or promoter components are not homogeneously distributed on a surface of each particle.

An average diameter of the spherical particles obtained by spray-drying is in the range from 50 to 80 μm, and more preferably in the range from 55 to 75 μm. When the average diameter of the particles is less than 50 μm, sometimes an average diameter of catalyst particles obtained by calcination step in the calcination step described above is less than 40 μm, and as a result the sufficient fluidity can not be obtained, or the catalyst loss may increase. When the average particle diameter is over 80 μm, sometimes an average diameter of particles of catalyst obtained by calcination in the calcination step may be over 75 μm, and sometimes the sufficient fluidity can not be obtained like when the average particle diameter is too small.

Diameters of the spherical particles are substantially homogeneously distributed, and a percentage of the particles with the diameter of less than 30 μm is preferably 10% by weight or less, and a percentage of the particles with the diameter over 90 μm is preferably 20% by weight or less. It is to be noted that particles with further different diameters may be classified.

The average particle diameter and the distribution of particle diameter can be measured, for instance, by the micro mesh sieve method.

Step (c)

The spherical particles obtained by spray-drying are then calcinated to provide a catalyst for oxychlorination.

A temperature for calcination is in the range from 350 to 850° C., and more preferably in the range from 500 to 700° C. When the temperature employed for calcination is less than 350° C., dehydration and crystallization of the pseudo-boehmite alumina are insufficient, and the activity and the selectivity are insufficient probably because binding to the activator component or promoter components in not adequate. When the temperature employed for calcination is over 850° C., copper, which is an activator component, is completely oxidized with the activity spoiled.

The time for calcination may be changed according to a temperature employed for calcination, and there is not specific restriction over the temperature. Generally the period of time required for calcination is in the range from 0.1 to 24 hours.

The catalyst for oxychlorination according to the present invention can be obtained as described above.

The obtained catalyst for oxychlorination contains copper by a content in the range from 5 to 20% by weight calculated as that of an oxide thereof (CuO), an alkaline-earth element by a content in the range from 0.1 to 6% by weight calculated as an oxide thereof, an alkali by a content in the range from 0.1 to 3% by weight calculated as an oxide thereof, a rare-earth element by a content in the range 0.1 to 6% by weight calculated as an oxide thereof, and alumina by a content in the range from about 60 to about 85% by weight. A content of chlorine in the catalyst is not more than 5% by weight.

The present invention is described below with reference to examples for the purpose of disclosure, but the present invention is not limited to the examples.

EXAMPLE 1

Preparation of Catalyst for Oxychlorination (1)
[Preparation of Slurry for Spray-Drying (1)]

74.7 kg of aqueous solution of sodium aluminate with the concentration of 5% by weight calculated as that of $Al_2O_3$ and 74.7 kg of aqueous solution of aluminum sulfate with the concentration of 2.5% by weight calculated as that of $Al_2O_3$ are mixed with each other to prepare alumina hydrogel slurry. A temperature employed for preparation of the alumina hydrogel slurry is 60° C., and pH is 9.5.

Then the alumina hydrogel slurry is filtered, cleaned with pure water at the temperature of 60° C. to obtain 5.60 kg of pseudo-boehmite alumina slurry with the concentration of 15% by weight calculated as $Al_2O_3$.

A portion of the pseudo-boehmite alumina slurry is dried, and observed with a scanning electron microscope to find that there are provided fibrous secondary particles comprising bundles of fibrous primary particles with the average length of 3 nm, and the average width of 1 nm.

0.31 kg of cupric nitrate trihydrate ($Cu(NO_3)_2.3H_2O$) with the concentration of 97% by weight, 0.04 kg of lanthanum nitrate hexahydrate ($La(NO_3)_3.6H_2O$) with the concentration of 99% by weight, 0.54 kg of cerium nitrate hexahydrate ($Ce(NO3)_3.6H_2O$) with the concentration of 98% by weight, and 0.20 kg of magnesium nitrate hexahydrate ($Mg(NO_3)_2.6H_2O$) with the concentration of 98% by weight are added in diluted nitric acid prepared by adding 0.10 kg of nitric acid with the concentration of 63% by weight in 0.38 kg of pure water, to prepare 1.07 kg of mixed nitrate aqueous solution with the concentration of 15% by weight calculated as that of [$Cuo+La_2O_3+Ce_2O_3+MgO$].

A temperature of the washed pseudo-boehmite alumina slurry is adjusted to 50° C., and then the mixed nitrate aqueous solution is mixed therein.

Then the mixed solution is homogenized with a homogenizer to prepare 6.67 kilograms of slurry for spray-drying (1). pH of the slurry is 3.5.

Testing for Corrosive Properties

A portion of the slurry for spray-drying (1) is put in a beaker, a flake of stainless steel is immersed in the slurry for spray-drying (1), the slurry is agitated for 10 days at the temperature of 50° C., then the flake is taken out and visually observed to assess the corrosive properties according to the following criteria. The result is shown together with characteristics of the slurry for spray-drying (1) in Table 1.

⊚: Luster on a surface with corrosion not recognized
○ Low luster on a surface with slight corrosion recognized
Δ: Low luster on a surface with corrosion clearly recognized
X: No luster on a surface with corrosion clearly recognized
[Preparation of Catalyst for Oxychlorination (1)]
Spray-drying The slurry for spray-drying (1) is sprayed into a heated air flow at the temperature of 220° C. to obtain spherical particles (1).

An average diameter of the spherical particles (1) is 65 μm, and a percentage of the particles with the diameter of 20 μm or below is 10% by weight, while that of the particles with the diameter of 149 μor more is 5% by weight.

Calcination

A catalyst for oxychlorination (1) is prepared by burning the spherical particles (1) for 0.5 hour at the temperature of 650° C. in a rotary calcination furnace.

The average diameter, CBD, crystal form of alumina, and composition of the catalyst for oxychlorination (1) are as shown in Table 2. In Table 2, a content of halogen is expressed by a percentage assuming that a total amount of oxides in the catalyst is 100% by weight.

Abrasion Resistance

Based on the method described in Japanese Patent No. 737,429, catalyst particles are flown under the conditions of catalyst fill ration of 50 g, nozzle diameter of 0.406 mm φ, and air flow rate of 0.425 $m^3$/hour, and weight percentages of the particles scattered from the fluidized bed vessel and recovered are measured at multiple time points for 15 hours from 5 hours until 20 hours after starting of flowing the sample, and a result is as shown in Table 2.

[Assessment of Catalytic Performance]

The activity and fluidity are assessed as described below, and the result is shown in Table 3.

Assessment of Activity 5 g of the catalyst for oxychlorination (1) is filled in a fixed fluidized bed reactor, and a nitrogen gas is supplied at a rate of 28.8 ml/min at the temperature of 230° C. to fluidize the catalyst. Then a mixed gas for reaction (containing ethylene by 39.2% by volume, hydrochloric acid by 46.1% by volume, and oxygen by 14.7% by volume) is supplied in place of the nitrogen gas at a rate of 62.5 ml/min. The space velocity (WHSV) is 750 (L/Hr/Kg Cat.) in this step.

The product gas is analyzed by means of chromatography. The activity, selectivity, yield and combustion property are as shown in Table 3.

Activity: Conversion rate of hydrochloric acid =(supplied hydrochloric acid—hydrochloric acid not reacted)/supplied hydrochloric acid×100 (mole %)

Selectivity: Selectivity for EDC=amount of EDC actually produced/amount of EDC theoretically produced×100 (mole %)

Yield (based on hydrochloric acid): Yield of EDC=Conversion rate of hydrochloric acid×Selectivity for EDC (mole %)

Combustion property: Combustion rate of ethylene=(CO+$CO_2$) moles/$C_2H_2$ moles×100 (mole %)

Assessment of Fluidity

During the reaction described above, a difference between a temperature at the bottom of the fluidized bed and a temperature at the top of the fluidized bed (ΔT: ° C.), and the difference is assessed based on the following references. The result is shown in Table 3.

⊚: ΔT is less than 3° C., and excellent fluidity is shown.
○: ΔT is 3° C. or more and less than 5° C., and relatively excellent fluidity is shown.
Δ: ΔT is 5° C. or more and less than 7° C., and the fluidity is acceptable.
X: ΔT is 7° C. or more, and the fluidity is not acceptable.

EXAMPLE 2

Preparation of Catalyst for Oxychlorination (2)
[Preparation of Slurry for Spray-drying (2)]

6.67 kg of the slurry for spray-drying (2) is prepared like in Example 1 excluding the point that 0.38 kg of pure water, 0.04 kg of lanthanum nitrate hexahydrate with the concentration of 99% by weight, and 0.04 kg of cerium nitrate hexahydrate with the concentration of 98% by weight are changed to 0.31 kg of pure water and 0.15 kg of rare-earth chloride solution with the concentration of 30% by weight. pH of the slurry is 3.5.

Testing for Corrosive Properties

Testing for the corrosive properties is performed like in Example 1, and the result is shown in Table 1.

[Preparation of the Catalyst for Oxychlorination (2)]

Spray-drying

The slurry for spray-drying (2) is sprayed into a heated air flow having the temperature of 220° C. to obtain spherical particles (2).

An average diameter of the spherical particles (2) is 65 μm, and a percentage of particles with the diameter of 20 μm or below is 10% by weight, while that of the particles with the diameter of 149 μm or more is 5% by weight.

Calcination

A catalyst for oxychlorination (2) is prepared by burning the spherical particles (2) for 0.5 hour at the temperature of 650° C. in a rotary calcination furnace.

An average diameter, CBD, crystal form of alumina, composition, and abrasion resistance of the catalyst for oxychlorination (2) are measured, and a result is shown in Table 2.

Assessment of Catalytic Performance

The catalytic performance of the catalyst for oxychlorination (2) is assessed like in Example 1 excluding the point that the catalyst for oxychlorination (2) is used in place of the catalyst for oxychlorination (1), and a result is as shown in Table 3.

EXAMPLE 3

Preparation of Catalyst for Oxychlorination (3)

[Preparation of Slurry for Spray-drying (3)]

6.67 kg of the slurry for spray-drying (3) is prepared like in Example 1 excluding the point that 0.38 kg of pure water, 0.04 kg of lanthanum nitrate hexahydrate with the concentration of 99% by weight, 0.04 kg of cerium nitrate hexahydrate with the concentration of 98% by weight, and 0.20 kg of magnesium nitrate hexahydrate with the concentration of 98% by weight are changed to 0.36 kg of pure water, 0.15 kg of rare-earth chloride solution with the concentration of 30% by weight, and 0.15 kg of magnesium chloride hexahydrate with the concentration of 98% by weight. pH of the slurry is 3.3.

Testing for Corrosive Properties

Testing for the corrosive properties is performed like in Example 1, and the result is shown in Table 1.

[Preparation of the Catalyst for Oxychlorination (3)]

Spray-drying

The slurry for spray-drying (3) is sprayed into a heated air flow having the temperature of 220° C. to obtain spherical particles (3).

An average diameter of the spherical particles (3) is 65 μm, and a percentage of particles with the diameter of 20 μm or below is 10% by weight, while that of the particles with the diameter of 149 μm or more is 5% by weight.

Calcination

A catalyst for oxychlorination (3) is prepared by burning the spherical particles (3) for 0.5 hour at the temperature of 650° C. in a rotary calcination furnace.

An average diameter, CBD, crystal form of alumina, composition, and abrasion resistance of the catalyst for oxychlorination (3) are measured, and a result is shown in Table 2.

Assessment of Catalytic Performance

The catalytic performance of the catalyst for oxychlorination (3) is assessed like in Example 1 excluding the point that the catalyst for oxychlorination (3) is used in place of the catalyst for oxychlorination (1), and a result is as shown in Table 3.

EXAMPLE 4

Preparation of Catalyst for Oxychlorination (4)

[Preparation of Slurry for Spray-drying (4)]

6.67 kg of the slurry for spray-drying (4) is prepared like in Example 1 excluding the point that 0.38 kg of pure water and 0.20 kg of magnesium nitrate hexahydrate with the concentration of 98% by weight are changed to 0.56 kg of pure water and 0.02 kg of potassium carbonate with the concentration of 99% by weight. pH of the slurry is 3.7.

Testing for Corrosive Properties

Testing for the corrosive properties is performed like in Example 1, and the result is shown in Table 1.

[Preparation of the Catalyst for Oxychlorination (4)]

Spray-drying

The slurry for spray-drying (4) is sprayed into a heated air flow having the temperature of 220° C. to obtain spherical particles (4).

An average diameter of the spherical particles (4) is 65 μm, and a percentage of particles with the diameter of 20 μm or below is 10% by weight, while that of the particles with the diameter of 149 μm or more is 5% by weight.

Calcination

A catalyst for oxychlorination (4) is prepared by burning the spherical particles (4) for 0.5 hour at the temperature of 650° C. in a rotary calcination furnace.

An average diameter, CBD, crystal form of alumina, composition, and abrasion resistance of the catalyst for oxychlorination (4) are measured, and a result is shown in Table 2.

Assessment of Catalytic Performance

The catalytic performance of the catalyst for oxychlorination (4) is assessed like in Example 1 excluding the point that the catalyst for oxychlorination (4) is used in place of the catalyst for oxychlorination (1), and a result is as shown in Table 3.

COMPARATIVE EXAMPLE 1

Preparation of Catalyst for Oxychlorination (R1)

[Preparation of Slurry for Spray-drying (R1)]

74.7 kg of aqueous solution of sodium aluminate with the concentration of 5% by weight calculated as that of $Al_2O_3$ and 74.7 kg of aqueous solution of aluminum sulfate with the concentration of 2.5% by weight calculated as that of $Al_2O_3$ are mixed with each other, to prepare alumina hydrogel slurry. The alumina hydrogel is prepared at the temperature of 60° C., and the pH is 9.5.

Then, the alumina hydrogel slurry is filtered, and is washed with pure water having the temperature of 60° C. to obtain 5.60 kg of pseudo-boehmite alumina slurry with the concentration of 15% by weight calculated as that of $Al_2O_3$.

A portion of the pseudo-boehmite alumina slurry is dried and is observed with a scanning electron microscope. There are provided fibrous secondary particles comprising bundle of fibrous primary particles with the average length of 3 nm and the average width of 1 nm.

0.27 kg of cupric chloride dehydrate with the concentration of 98% by weight, 0.18 kg of rare-earth chloride solution with the concentration of 30% by weight, and 0.16 kg of magnesium chloride hexahydrate with the concentration of 98% are dissolved in diluted hydrochloric acid prepared in adding 0.11 kg of hydrochloric acid with the concentration of 35% by weight in 1.24 kg of pure water, to prepare 1.96 kg of aqueous solution of mixed hydrochloric salt with the concentration of 15% by weight calculated as that of [$CuO+La_2O_3+Ce_2O_3+MgO$].

A temperature of the pseudo-boehmite alumina slurry washed as described above is adjusted to 50° C., and then the aqueous solution of mixed hydrochloric salt is added therein.

Then the mixed slurry is homogenized with a homogenizer to prepare 7.56 kg of slurry for spray-drying (R1). pH of the slurry is 3.2.

Testing for Corrosive Properties

The testing for corrosive properties is performed like in Example 1, and a result is shown in Table 1.

[Preparation of Catalyst for Oxychlorination (R1)]
Spray-drying

The slurry for spray-drying (R1) is sprayed into a heated air flow having the temperature of 220° C. to obtain spherical particles (R1).

An average diameter of the spherical particles (RI) is 65 μm, and a percentage of particles with the diameter of 20 μm or below is 10% by weight, while that of the particles with the diameter of 149 μm or more is 5% by weight.

Calcination

A catalyst for oxychlorination (R1) is prepared by burning the spherical particles for 0.5 hour at the temperature of 550° C. in a rotary calcination furnace.

An average diameter, CBD, crystal form of alumina, composition, and abrasion resistance of the catalyst for oxychlorination (R1) are measured, and a result is shown in Table 2.

Assessment of Catalytic Performance

The catalytic performance of the catalyst for oxychlorination (R1) is assessed like in Example 1 excluding the point that the catalyst for oxychlorination (R1) is used in place of the catalyst for oxychlorination (1), and a result is as shown in Table 3.

Comparative Example 2

Preparation of Catalyst for oxychlorination (R2)
[Preparation of Slurry for Spray-drying (R2)]

7.56 kg of the slurry for spray-drying (R2) is prepared like in Example 1 excluding the point that 1.24 kg of pure water and 0.16 kg of magnesium chloride hexahydrate with the concentration of 98% by weight are changed to 1.38 kg of pure water and 0.02 kg of potassium chloride with concentration of 97% by weight. pH of the slurry is 3.4.

Testing for Corrosive Properties

The testing for corrosive properties is performed like in Example 1, and a result is shown in Table 1.

[Preparation of Catalyst for Oxychlorination (R2)]
Spray-drying

The slurry for spray-drying (R2) is sprayed into a heated air flow having the temperature of 220° C. to obtain spherical particles (R2).

An average diameter of the spherical particles (R2) is 65 μm, and a percentage of particles with the diameter of 20 μm or below is 10% by weight, while that of the particles with the diameter of 149 μm or more is 5% by weight.

Calcination

A catalyst for oxychlorination (R2) is prepared by burning the spherical particles (R2) for 0.5 hour at the temperature of 550° C. in a rotary calcination furnace.

An average diameter, CBD, crystal form of alumina, composition, and abrasion resistance of the catalyst for oxychlorination (R2) are measured, and a result is shown in Table 2.

Assessment of Catalytic Performance

The catalytic performance of the catalyst for oxychlorination (R2) is assessed like in Example 1 excluding the point that the catalyst for oxychlorination (R2) is used in place of the catalyst for oxychlorination (1), and a result is as shown in Table 3.

TABLE 1

| | Slurry for spray-drying | | | | | | |
|---|---|---|---|---|---|---|---|
| | Pseudo-boehmite slurry | | | | | | |
| | Primary particle | | | | Concentration | Halogen | Corrosive |
| | Length nm | Width nm | Conc. Wt % | pH | of solid phase Wt % | content Wt % | property against steel |
| Ex1 | 3 | 1 | 15 | 3.5 | 15 | — | ◎ |
| Ex2 | ↑ | ↑ | ↑ | 3.5 | ↑ | 0.3 | ○ |
| Ex3 | ↑ | ↑ | ↑ | 3.3 | ↑ | 1.1 | ○ |
| Ex4 | ↑ | ↑ | ↑ | 3.7 | ↑ | — | ◎ |
| CE1 | 3 | 1 | 15 | 3.2 | 15 | 7.6 | X |
| CE2 | ↑ | ↑ | ↑ | 3.4 | ↑ | 7.0 | X |

TABLE 2

| | Catalysts | | | | | | | | | |
|---|---|---|---|---|---|---|---|---|---|---|
| | | Ave. par. | Abrasion Resist. | Copper | Alk-earth | Rare-earth oxide | | Alk. | Alumina | |
| | CBD ml/g | diameter μm | Wt %/ 15 Hr | oxide Wt % | oxide Wt % | $La_2O_3$ Wt % | $Ce_2O_3$ Wt % | oxide Wt % | Crystal form | Wt % | Halogen Wt % |
| Ex1 | 1.05 | 60 | 0.5 | 10.0 | 3.0 | 1.5 | 1.5 | — | γ | 84.0 | — |
| Ex2 | 1.07 | ↑ | 0.3 | ↑ | ↑ | ↑ | ↑ | — | ↑ | ↑ | 0.1 |
| Ex3 | 1.11 | ↑ | 0.2 | ↑ | ↑ | ↑ | ↑ | — | ↑ | ↑ | 0.5 |
| Ex4 | 1.05 | ↑ | 1.2 | ↑ | — | ↑ | ↑ | 1.0 | ↑ | 86.0 | — |
| CE1 | 1.25 | 60 | 0.6 | 10.0 | 3.0 | 1.5 | 1.5 | — | γ | 84.0 | 6.8 |
| CE2 | 1.20 | ↑ | 0.9 | ↑ | — | ↑ | ↑ | 1.0 | ↑ | 86.0 | 6.2 |

TABLE 3

| | Catalytic performance | | | | |
| --- | --- | --- | --- | --- | --- |
| | Conversion rate of HCl mol % | Selectivity for EDC mol % | Combustion rate of ethylene mol % | EDC yield mol % | Fluidity |
| Ex1 | 99.7 | 99.8 | 2.2 | 97.30 | ⊚ |
| Ex2 | 99.6 | 99.6 | 2.2 | 97.00 | ⊚ |
| Ex3 | 99.5 | 99.5 | 2.3 | 96.70 | ⊚ |
| Ex4 | 99.6 | 99.7 | 2.5 | 96.80 | ○ |
| CE1 | 99.3 | 99.6 | 2.3 | 96.6 | Δ |
| CE2 | 99.5 | 99.5 | 2.5 | 96.5 | Δ |

What is claimed is:

1. A method of producing a catalyst for oxychlorination comprising alumina and copper, the method comprising the following steps (a) to (c):
   (a) preparing a slurry for spray-drying by adding, to a pseudo-boehmite alumina slurry, nitric acid in a range from 0.001 to 0.1 moles per mole of $Al_2O_3$ in the slurry, and an aqueous solution of cupric nitrate;
   (b) spray-drying the slurry; and
   (c) calcining particles obtained in the step (b),
   wherein a content of copper is in the range from 5 to 20% by weight calculated as CuO, and a content of chlorine is 0.5% by weight or less.

2. The method of producing the catalyst for oxychlorination according to claim 1, wherein pH of the slurry for spray-drying is in the range from 3 to 5.

3. The method of producing the catalyst for oxychlorination according to claim 1, wherein an aqueous solution of an alkaline earth metal nitrate is added in the step (a).

4. The method of producing the catalyst for oxychlorination according to claim 1, wherein an aqueous solution of a rare earth metal nitrate is added in the step (a).

5. The method of producing the catalyst for oxychlorination according to claim 1, wherein an aqueous solution of an alkaline metal nitrate is added in the step (a).

6. The method of producing the catalyst for oxychlorination according to claim 1, wherein the nitric acid has a concentration in a range of 10 to 35% by weight, and a pH of the pseudo-boehmite alumina slurry is in a range from 2 to 6.

7. A method of producing a catalyst for oxychlorination, comprising the steps (a) to (d):
   (a) preparing a slurry for spray-drying by adding, to a pseudo-boehmite alumina slurry, nitric acid in a range from 0.001 to 0.1 moles per mole of $Al_2O_3$ in the slurry, and an aqueous solution of cupric nitrate;
   (b) adding to the slurry an alkaline earth metal salt, a rare earth metal salt and an alkaline salt;
   (c) spray-drying the slurry; and
   (d) calcining particles obtained in the step (c),
   wherein the catalyst consists essentially of alumina; copper in a range from 5 to 20% by weight calculated as CuO; the alkaline earth metal salt in a range from 0.1 to 6% by weight; the rare earth meal salt in a range from 0.1 to 6% by weight; and the alkaline salt in a range from 0.1 to 3% by weight, and a content of chlorine in the catalyst is 0.5% by weight or less.

8. The method of producing the catalyst for oxychlorination according to claim 7, wherein a pseudo-boehmite alumina has an average length in a range from 1 to 10 nm, and an average width in a range from 0.5 to 3 nm.

9. The method of producing the catalyst for oxychlorination according to claim 8, wherein spherical particles are obtained by spraying-drying the slurry, said spherical particles having an average diameter in a range from 50 to 80 μm.

10. The method of producing the catalyst for oxychlorination according to claim 9, wherein the spherical particles are calcined in a range from 350 to 850 °C.

11. The method of producing the catalyst for oxychlorination according to claim 7, wherein the nitric acid has a concentration in a range of 10 to 35% by weight, and a pH of the pseudo-boehmite alumina slurry is in a range from 2 to 6.

12. A method of producing a catalyst for oxychlorination, comprising the steps (a) to (d):
   (a) preparing a slurry for spray-drying by adding, to a pseudo-boehmite alumina slurry, nitric acid in a range from 0.001 to 0.1 moles per mole of $Al_2O_3$ in the slurry, and an aqueous solution of cupric nitrate;
   (b) adding to the slurry an alkaline earth metal salt, a rare earth metal salt and an alkaline salt;
   (c) spray-drying the slurry; and
   (d) calcining particles obtained in the step (c),
   wherein the catalyst consists essentially of alumina; copper in a range from 5 to 20% by weight calculated as CuO; the alkaline earth metal salt in a range from 0.1 to 6% by weight; the rare earth meal salt in a range from 0.1 to 6% by weight; and the alkaline salt in a range from 0.1 to 3% by weight, and a content of chlorine in the catalyst is 0.5% by weight or less, and
   wherein chlorine is substantially absent in the catalyst.

* * * * *